(12) United States Patent
Schutz et al.

(10) Patent No.: US 8,926,591 B2
(45) Date of Patent: Jan. 6, 2015

(54) IMPLANTABLE VASCULAR ACCESS

(75) Inventors: Daniel Schutz, Aarwangen (CH); Jean-Marc Guenat, Bienne (CH); Adrian Auderset, Nidau (CH); Christof Stieger, Cambridge, MA (US); Felix Frey, Kriechenwil (CH); Rudolf Hausler, Bolligen (CH)

(73) Assignee: Cendres + Metaux SA, Bienne (CH)

( * ) Notice: Subject to any disclaimer, the term of this patent is extended or adjusted under 35 U.S.C. 154(b) by 340 days.

(21) Appl. No.: 13/401,508

(22) Filed: Feb. 21, 2012

(65) Prior Publication Data

US 2012/0157924 A1 Jun. 21, 2012

Related U.S. Application Data

(63) Continuation of application No. PCT/EP2010/062091, filed on Aug. 19, 2010.

(30) Foreign Application Priority Data

Aug. 21, 2009 (EP) .................................... 09168432

(51) Int. Cl.
| | | |
|---|---|---|
| A61M 25/16 | (2006.01) | |
| A61M 25/18 | (2006.01) | |
| A61M 39/02 | (2006.01) | |
| A61M 5/178 | (2006.01) | |
| A61M 5/32 | (2006.01) | |
| A61M 39/26 | (2006.01) | |
| A61M 1/36 | (2006.01) | |

(52) U.S. Cl.
CPC ........... *A61M 39/0247* (2013.01); *A61M 39/26* (2013.01); *A61M 1/3653* (2013.01); *A61M 2039/025* (2013.01)
USPC ............................ 604/539; 604/183; 604/174

(58) Field of Classification Search
CPC ................. A61M 39/0247; A61M 2039/0258; A61M 2039/0261; A61M 2039/0264; A61M 2039/0282; A61M 2039/025
USPC ......... 604/174, 533–539, 6.16, 175, 181, 183
See application file for complete search history.

(56) References Cited

U.S. PATENT DOCUMENTS

| 4,421,507 A | 12/1983 | Bokros |
|---|---|---|
| 4,581,020 A | 4/1986 | Mittleman |

(Continued)

FOREIGN PATENT DOCUMENTS

| WO | WO-97/49438 A1 | 12/1997 |
|---|---|---|
| WO | WO-03/086527 A1 | 10/2003 |

(Continued)

*Primary Examiner* — Rebecca E Eisenberg
(74) *Attorney, Agent, or Firm* — Blank Rome LLP

(57) ABSTRACT

A transcutaneous implantable access port for removal and/or return of fluids of a patient comprises a fixation unit adapted to be fixed to a bone of the patient; a valve unit comprising a sealing membrane at its distal end and one or more chambers; an internal conduit fluidly connectable to vascular structure of the patient and releasably connectable to the valve unit to establish fluidic communication between the internal conduit and said one or more chambers; and an extracorporeal connecting member having an end portion. The extracorporeal connecting member is connectable to the distal end of the valve unit, opening and closing a fluidic passage between the connecting member and said one or several chambers when the connecting member is respectively connected to the access port and withdrawn therefrom. The access port can be used for high volume removal and/or return of blood or other fluids from the patient.

16 Claims, 3 Drawing Sheets

(56) References Cited

U.S. PATENT DOCUMENTS

| | | | |
|---|---|---|---|
| 5,098,397 | A | 3/1992 | Svensson et al. |
| 8,216,191 | B2 * | 7/2012 | Horiguchi .................... 604/175 |
| 2006/0047249 | A1 | 3/2006 | Shubayev et al. |
| 2011/0034852 | A1 * | 2/2011 | Hausler et al. ............... 604/6.16 |

FOREIGN PATENT DOCUMENTS

| | | |
|---|---|---|
| WO | WO-2005/023336 A2 | 3/2005 |
| WO | WO-2007/051339 A1 | 5/2007 |
| WO | WO-2007/087460 A2 | 8/2007 |

* cited by examiner

IMPLANTABLE VASCULAR ACCESS

RELATED APPLICATIONS

This application is a continuation of Application No. PCT/EP2010/062091 (WO 2011/020873) filed Aug. 19, 2010, which claims priority to EP09168432.4, filed Aug. 21, 2009, the contents of both of which is hereby incorporated in its entirety by reference.

FIELD

The present disclosure relates to an implantable vascular access for removal and/or return of fluids to a patient. The implantable access is usable for establishing temporary access to an animal's (including human) blood vessels, an organ, a body lumen or cavity or any combination thereof for the purpose of hemodialysis, drug delivery, nutrition delivery, urinary catheterism or any other supply or removal of fluids.

BACKGROUND

Access to a patient's lumen can be established by a variety of temporary and permanently implanted devices. However, despite several types of lumen access ports and devices proposed over recent years, body lumen access remains one of the most problematic areas in the treatment of patients requiring long-term access. Most simply, temporary access can be provided by the direct percutaneous introduction of a needle through the patient's skin and into a blood vessel. While such a direct approach is relatively straightforward and suitable for applications such as intravenous feeding, short term intravenous drug delivery and other applications which are limited in time, they are not suitable for hemodialysis and other extracorporeal procedures that must be repeated periodically and often for the patient's lifetime.

Haemodialysis patients commonly undergo a placement of one of the two, or both, widely accepted long-term vascular access options during the term of their treatment. It is estimated that 50% of hospitalization time of haemodialysis patients is related to problems of access to the vascular system of the human body.

On the one hand, WO 2005/023336 discloses a surgical placement of an arteriovenous synthetic graft connecting a patient's adjacent peripheral artery and vein to divert some of the arterial blood flow through the graft. The other is an arteriovenous fistula, a direct surgical connection between adjacent artery and vein with no synthetic conduit used. In both cases, the blood circulation is accessed with two needles inserted through the skin into either the synthetic graft in the former case, or the venous portion of an arteriovenous fistula in the latter scenario. Needle stick injuries and infections contribute to the loss of these types of accesses.

US 2006/0047249, by Shubayev and Elyav, proposes a percutaneous vascular access system. This system consists of a cylindrical device body having a pair of hollow nipples extending from the exterior to the interior and a rotatable inner core with two positions to open and close the connections. However, the fixation of such a device to the skin or other soft tissue of the body, i.e. as a tissue anchor according to US 2006/0047249, raises a number of problems, such as the danger of displacement during use caused by body movements or exposure to mechanic stress.

Bone implanted access devices have also be proposed. For example, WO 2007/051339 concerns an access port comprising a central cylindrical portion, and external and internal canal communicating through a valve. Here, the access port contains only one fluid canal and is destined to be implanted in a tooth-supporting bone.

SUMMARY

The present application discloses a transcutaneous implantable access port which overcome at least some limitations of the prior art.

According to the embodiments, a transcutaneous implantable access port for removal and/or return of fluids of a patient can comprise: a fixation unit adapted to be fixed to a bone of the patient; a valve unit comprising a sealing membrane at its distal end and one or more chambers adjacent of said sealing membrane, the valve unit being detachably mounted on the fixation unit such that the distal end of the valve unit protrudes extracorporealy; an internal conduit fluidly connectable to a vascular structure of the patient and releasably connectable to the valve unit such as to establish fluidic communication between the internal conduit and said one or more chambers; and an extracorporeal connecting member having an end portion; wherein said extracorporeal connecting member is adapted to be connected to the distal end of the valve unit such that said end portion passes through said sealing membrane such as to open a fluidic passage between the connecting member and said one or several chambers and whereby said fluidic passage closes, when the connecting member is respectively connected to the access port and withdrawn therefrom.

In an embodiment, the access port can further comprise an aligning device arranged for inserting the end portion in said one or several chambers according to a predetermined insertion distance, when said extracorporeal connecting member is connected to the valve unit.

In another embodiment, said aligning device can comprise a guiding element adapted to align the portion of said one or more access lines relative to said one or several chambers, respectively.

In yet another embodiment, said guiding element is a guiding cap containing one or several guiding passages aligned with each of said one or several chambers.

In yet another embodiment, said one or several guiding passages have a tapered shape.

In yet another embodiment, said aligning device comprises a locking device attached to the connecting member.

In yet another embodiment, said locking device comprises a locking member having a locking end adapted to slidably engage along the lateral periphery of the valve unit.

In yet another embodiment, said sealing membrane is made of silicone rubber or a self-repairing polymer.

In yet another embodiment, said sealing membrane comprises one or several preformed passage, each of said one or several preformed passages being connected with one of said one or several chambers, respectively.

In yet another embodiment, said aligning device is adapted to align the end portion relative to one of said one or several preformed passages, respectively.

In yet another embodiment, said internal conduit contains one or more tube lines, each of said one or more tube lines being fluidly connected to one of said one or more chambers, respectively.

In yet another embodiment, said extracorporeal connecting member is adapted to be connected to an extracorporeal conduit comprising one or several access lines in fluid communication with the end portion, respectively.

In yet another embodiment, the fixation unit is a base plate or comprises a three-dimensional structure.

In yet another embodiment, said end portion comprises a cannula.

The transcutaneous implantable access port disclosed herein provide a bone anchored access port that may be used for high volume removal and/or return of blood or other fluids from the animal's (including human) body undergoing an extracorporeal blood therapy such as hemodialysis, hemofiltration, hemodiafiltration, apheresis, or a drug therapy, or a non-oral nutrition, or urinary catheterism or the like, with good stability and less risk of infection. Although the access port disclosed herein is particularly useful for establishing vascular access, it will also be useful for accessing other body lumens and cavities, such as the peritoneal cavity and the like.

In the present disclosure, the expressions "proximal" signify the side of the access port being directed towards the patient's body, while the expression "distal" signifies the opposite side.

BRIEF DESCRIPTION OF THE DRAWINGS

The preferred embodiments will be better understood with the aid of the description of an embodiment given by way of example and illustrated by the figures, in which.

DETAILED DESCRIPTION OF PREFERRED EMBODIMENTS

Figure 1:
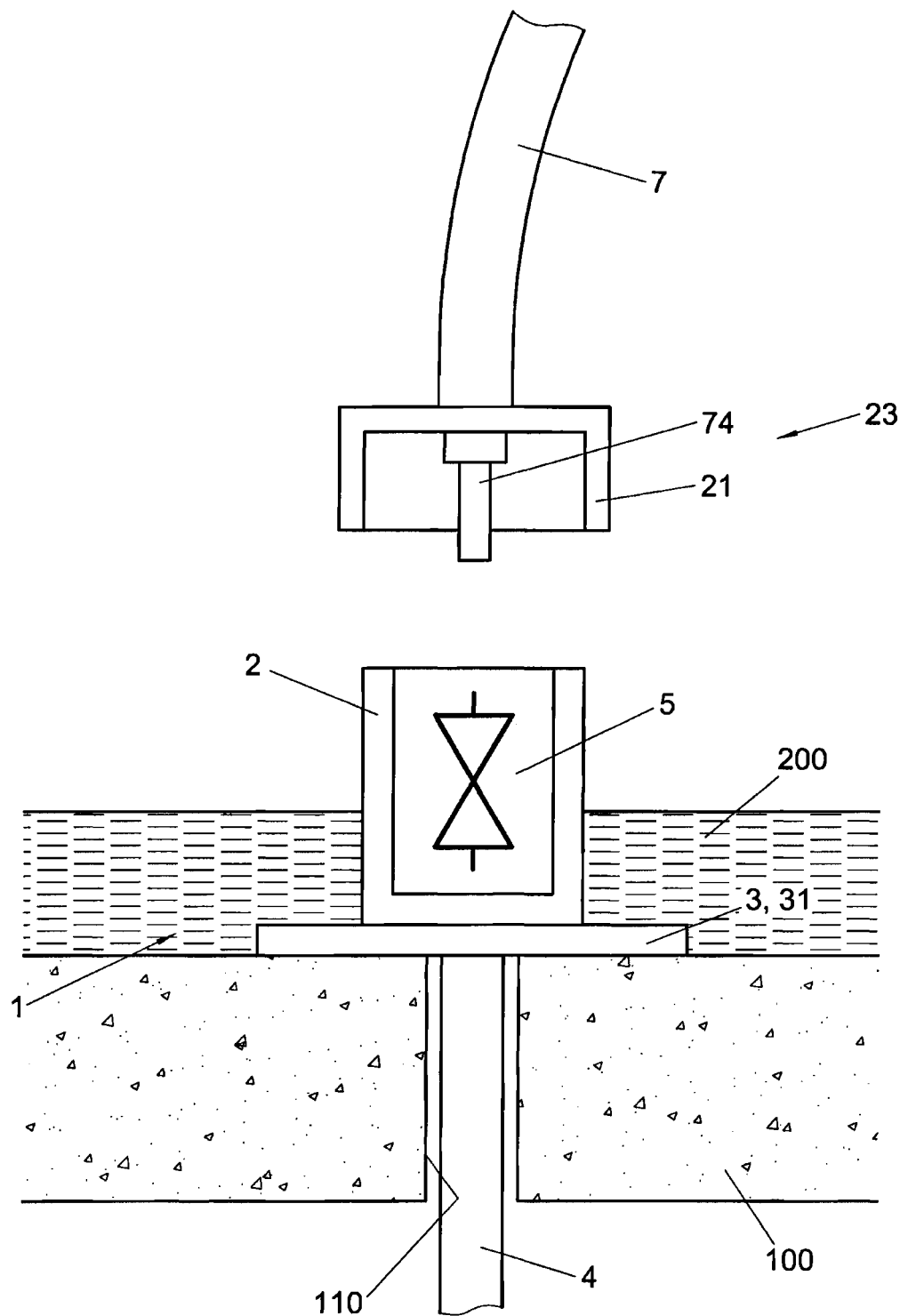
FIG. 1 shows a schematic view of an access port system comprising a transcutaneous implantable access port and an extracorporeal conduit.

FIG. 1 illustrates a schematic view of the functional parts of an access port system for removal and/or return of fluids to a patient, according to an embodiment. The access port system comprises a transcutaneous implantable access port 1 containing a valve unit 5, a fixation unit 3, and an internal conduit 4 connected to the valve unit 5. The valve unit 5 is fixed, preferably releasably, to the fixation unit 3. The access port 1 can also comprise a casing 2 fixed to the fixation unit 3, the valve unit 5 being disposed fixedly in the casing 2, as shown in the example of FIG. 1. The fixation unit 3 can be permanently anchored to a bone 100 such as hip, clavicle, sternum or any other section of the skeleton. Preferably, the fixation device 3 is permanently anchored to the mastoid, temporal or parietal bone. In the example of FIG. 1, the fixation unit comprises a base plate 31 and anchoring can be performed with screws (not shown). In FIG. 1, the base plate 31 is shown anchored at the surface of the bone 100 but could also be at least partly entrenched in the bone 100. Anchoring can also be performed using pins, wires, non-absorbable threads, cement or any other suitable fixation means.

In a preferred embodiment, the access port 1 is anchored such as the valve unit 5, and possibly the casing 2, perforate the skin 200 in order to provide a direct extracorporeal access to at least a portion of the valve unit 5. The valve unit 5 is detachably mounted on the fixation unit 3, 31, 33 such that the distal end of the valve unit 5 protrudes extracorporealy.

As shown in FIG. 1, the access port system also comprises an extracorporeal conduit 7, containing one or several access lines 71, 72 passing within the extracorporeal conduit 7 (see FIG. 2), and a connecting portion, or extracorporeal connecting member 23, at one of its extremity. The connecting member 23 comprises a portion the one or several access lines 71, 72, one such portion, or end portion 74, being shown in FIG. 1. Preferably, the extracorporeal connecting member 23 is adapted to be connected to the extracorporeal conduit 7 comprising one or several access lines 71, 72, each of one or several access lines 71, 72 being in fluid communication with the end portion 74, 75, respectively.

The extracorporeal conduit 7 can be possibly connected, to its other extremity, to a haemodialysis system, repositories for drug or nutrition delivery, bags for urinary catherism and the like. The internal conduit 4 can be flexible and can pass subcutaneously or through a hole 110 drilled in the bone 100, before penetrating soft tissue and/or being connected to a vascular structure of the patient. For example, the proximal tip of the internal conduit 4 can be connected to a body lumen by simple perforation, sewing, gluing and the like.

Figure 2:
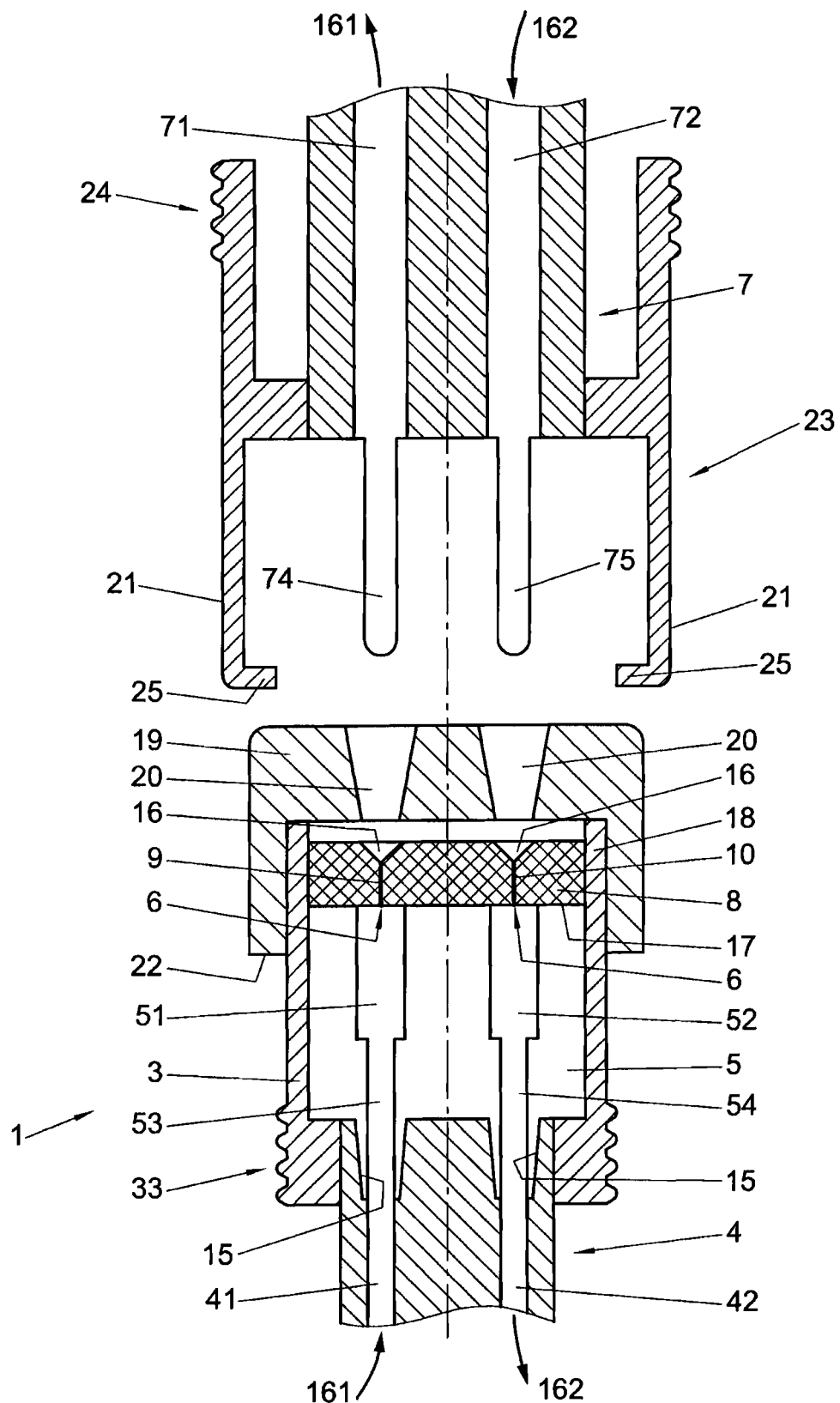
FIG. 2 illustrates a detailed view of the access port system according to an embodiment.

FIG. 2 shows a detailed view of the access port system, according to an embodiment of the invention. In the embodiment of FIG. 2, the fixation unit 3 has a generally cylindrical shape and comprises a three-dimensional structure, here a threaded structure 33, on the lower portion of the fixation unit external surface. The fixation of the access port 1 comprises the drilling of the hole 110 (see FIG. 1) in the bone 100 for introduction of the hollow fixation unit 3. Alternatively, the three-dimensional structure can be roughened structure (not shown). More generally, the three-dimensional structure can be provided with a lathe, a mechanical treatment such as sandblasting, or using a chemical or electrochemical etching treatment or a combination of at least two of these treatments. In order to facilitate its osseointegration, the three-dimensional structure can be coated with biocompatible, artificially produced bonelike substances, such as calcium sulfate or hydroxyapatite, for example, by coating the material by plasma spraying.

In the example of FIG. 2, the valve unit 5 is disposed within the fixation unit 3. The valve unit can be releasably fixed to the fixation unit 3 using threads or any other fixation means. Here, the valve unit 5 comprises a first chamber 51 and a second chamber 52, the first and second chambers 51, 52 respectively fluidly connected to a first and a second channel 53, 54 extending below the chambers 51, 52. The valve unit 5 disclosed herein is not limited to a configuration comprising two chambers 51, 52, but also comprises the valve unit 5 comprising one or more chambers 51, 52.

The internal conduit 4 can comprise one or more tube lines 41, 42, each of the one or more tube lines 41, 42 being fluidly connected to one of said one or more chambers 51, 52 of the valve unit 5. The internal conduit 4 can be further fluidly connectable to a vascular structure of the patient and releasably connectable to the valve unit 5, such as to establish fluidic communication between the internal conduit 4 and said one or more chambers 51, 52. In the example of FIG. 2, the internal conduit 4 comprises a first and a second tube line 41, 42 and can be permanently air- and waterproof attached to the valve unit 5 to establish fluidic communication between the first and second tube lines 41, 42 and the first and second chambers 51, 52, via the first and second channel 53, 54, respectively. As represented in FIG. 2, the first and second tube lines 41, 42 are tightly fitted on chuck cones 15 provided by the downward extension of the first and a second channel 53, 54. Alternatively, the first and second chambers 51, 52 can extend down the chuck cones 15 and be fluidly connected directly to the first and second tube line 41, 42, respectively.

The internal conduit 4, encompassed by the fixation unit 3, can be locked in its attached position using clamping structures (not shown) or by gluing, or the like. Barbs (also not shown) can be provided on the outer surface of the chuck cones 15, the internal conduit 4 being slipped over the outer surface of the chuck cones 15 with the barbs tending to keep the internal conduit 4 to the chuck cones 15. Alternatively, a single chuck cone (not represented) comprising the two channels 53, 54, or the two chambers 51, 52, can be used for attaching the internal conduit 4. The internal conduit 4 can also be connected to the valve unit 5 using a pipe coupling connector, such as a threaded coupling, basquill lock and the like.

During the assembly of the access port 1, the internal conduit 4 can be placed in the fixation unit 3 after introduction of the latter but before being fixed to the valve unit 5.

The valve unit 5 further comprises a sealing membrane 8 at its distal end, the sealing membrane 8 being adjacent to the one or several chambers 51, 52. In the example of FIG. 2, the valve unit 5 the sealing membrane 8 is disposed on the upper flat surface of the valve 5, more particularly in a seat 17 delimited by the upper flat surface of the valve 5 and the upper cylindrical end 18 of the fixation unit 3, projecting upwardly above the membrane top surface. Preferably, the membrane 8 has a cylindrical shape, conformal with the seat 17, in order to be tightly fitted within the seat 17 and seal open ends 6 of the first and second chamber 51, 52. Alternatively, the top surface of the membrane 8 can lie above the upper end 18 of the fixation unit 3.

A detailed view of the extracorporeal conduit 7 and the connecting member 23 according to an embodiment is also represented in FIG. 2. In this example, the extracorporeal conduit 7 comprises a first and a second access line 71, 72. The connecting member 23 comprises a first portion, or first cannula 74, of the first access line 71 and second portion, or second cannula 75, the second access line 72. The first and second cannulas 74, 75 are shown rounded or blunted at their proximal extremity, i.e., the extremity penetrating the sealing membrane 8. Other shapes of the first and second cannulas proximal extremity are also possible. For example, the first and second cannulas proximal extremity can be tip-shaped. Alternatively, the first and second end portions, or cannulas 74, 75, can be needle shaped.

In FIG. 2, the arrows 161 and 162 designate possible flow directions of the blood within, respectively, the access lines 71, 72 and tube lines 41 and 42, in an exemplary haemodialysis application. In this example, the first tube line 41 and access line 71 are used for removal of blood to be dialyzed. The dialyzator (not shown) is connected to the access port 1 via the extracorporeal conduit 7. Dialyzed blood is returned via the second access line 72 into the second tube line 42.

In an embodiment, the extracorporeal connecting member 23 is adapted to be connected to the distal end of the valve unit 5 such that said end portion 74, 75 passes through said sealing membrane 8 such as to open a fluidic passage between the connecting member 23 and said one or several chambers 51, 52 when the connecting member 23 is connected to the access port 1. When the connecting member 23 is withdrawn from the access port 1, the sealing membrane 8 reseals and the fluidic passage closes.

In an embodiment, the connecting member 23 is connected to the extracorporeal conduit 7 and, during connection of the connecting member 23 to the access port 1, the sealing membrane 8 is penetrated by the first and second cannulas 74, 75, the sealing membrane 8 being adapted to open by deformation during the passage of the two cannulas 74, 75. Once the first and second cannulas 74, 75 have penetrated the sealing membrane 8, fluidic communication is established between the first and second access lines 71, 72 and the first and second chambers 51, 52, respectively. The sealing membrane 8 is adapted to seal, or at least substantially seal, the passages around the cannulas 74, 75 when they are inserted, and to be resealed after removal of the cannulas 74, 75. To this end, the sealing membrane 8 can be made from a variety of suitable flexible and resilient materials including biocompatible elastomers such as silicone rubber or self-repairing polymers. The sealing membrane 8 thickness can be selected to provide sufficient flexibility to allow the sealing membrane 8 to separate as the cannulas 74, 75 are inserted into it.

In an embodiment, the sealing membrane 8 comprises one or several preformed passage 9, 10, each of said one or several preformed passages 9, 10 being connected with one of said one or several chambers 51, 52, respectively. As shown in FIG. 2, the sealing membrane 8 is provided with a first and a second preformed passage 9, 10 extending through the membrane 8, the first preformed passage 9 being aligned with the first chamber 51 and the second preformed passage 10 being aligned with the second chambers 52. Here, during connection of the extracorporeal conduit 7, the first and second cannulas 74, 75 are inserted through the first and second preformed passages 9, 10, respectively. The upper end of the first and second passages 9, 10 can comprise a dimple 16 as reflected in FIG. 2. Such dimples 16 help guiding the cannulas 74, 75 into the passages 9, 10, as the cannulas proximal extremity first come with upper surface of the sealing membrane 8.

In another embodiment, the extracorporeal connecting member 23 further comprises an aligning device 19, 21 arranged for inserting the end portion 74, 75 in said one or several chambers 51, 52 according to a predetermined insertion distance, when the extracorporeal connecting member 23 is connected to the valve unit 5.

In a variant of the embodiment, the aligning device comprises a guiding element 19 adapted to align the first and second cannula 74, 75 relative to the first and second chamber 51, 52, respectively. In the example of FIG. 2, the guiding element is a guiding cap 19, for example, threadingly engaged on the upper portion of the fixation unit 3 or by any other fixation means, the guiding cap 19 comprising one or several guiding passages 20, two in the example of FIG. 2, each guiding passage 20 being axially aligned with the first and second chamber 51, 52, and/or with the preformed passages 9, 10. The guiding passages 20 can be advantageously used for guiding accurately the first and second cannulas 74, 75 with the first and second chamber 51, 52 and/or the first and second preformed passages 9, 10, respectively, during connection of the extracorporeal conduit 7 on the access port 1. Moreover, the guiding passages 20 can be arranged such that the end portions 74, 75 can be inserted through the sealing membrane 8 and in the one or several chambers 51, 52 according to the predetermined insertion distance. For example, the guiding passages 20 and the end portions 74, 75 can have a similarly tapered shape. When the end portions 74, 75 are inserted into the guiding passages 20, increasing mutual contact area between the tapered shapes of the end portions and guiding passages prevents the end portions 74, 75 penetrating within the one or several chambers 51, 52 farther than the predetermined insertion distance. In another embodiment, the sealing membrane 8 can be radially compressed as the guiding cap 19 is engaged on the fixation unit 3. The radial compressive force exerted by the guiding cap 19 on the sealing membrane 8 can help sealing the membrane and/or the two preformed passages 9, 10 in the absence of the cannulas 74, 75. The guiding cap 19 can also be used to compress the sealing membrane 8 axially to ensure a good sealing between the sealing membrane 8 and the chambers 51, 52. The axial compressive forces exerted by the guiding cap 19 can also cause the sealing membrane material surrounding the preformed passages 9, 10 to tightly close, improving the seal of the passages 9, 10 after removal of the cannulas 74, 75.

Figure 3:
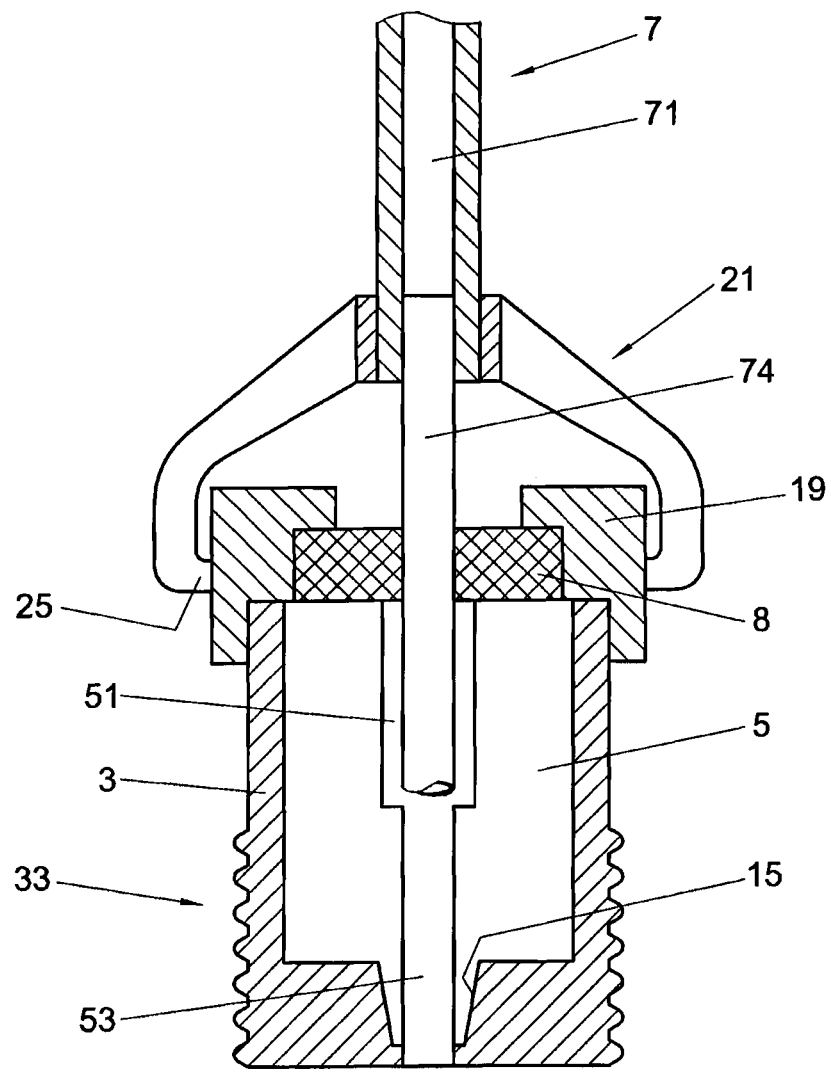
FIG. 3 illustrates the access port system according to another embodiment.

In another variant of the embodiment, the sealing membrane 8 can be confined by the inner wall of the guiding cap 19, as represented in FIG. 3.

In another embodiment not represented, a protection cap or any other covering element may be inserted on top of the valve unit 5 when the access port 1 is not used, to prevent mechanical stress, damage, as well as external contamination. Alternatively, sealing plugs may be inserted into the guiding passages 20 of the guiding cap 19 when the access port 1 is unused.

In yet another embodiment not represented, separate sealing membranes can be used to seal each chambers 51, 52. Here, each sealing membrane can comprise a preformed passage.

In yet another embodiment, the aligning device comprises a locking device 21 attached to the connecting member 23 and being arranged such as to slidably engage along the lateral periphery of the valve unit 5, or along the lateral periphery of the casing or the guiding cap 19. The locking device 21 can also be used for firm attachment of the extracorporeal conduit 7, or connecting member 23 to the access port 1 and/or avoiding the accidental removal of the conduit 7, or connecting member 23. In the example of FIG. 2, the locking device consists of two flexible locking members 21 attached opposite on the extracorporeal member 23 and adapted to slidably engage their curved locking ends 25 along the lateral periphery of the cap 19. The locking ends 25 get locked at a predetermined position, corresponding to the locking ends 25 being engaged with the lower projecting edge 22 of the guiding cap 19, when the extracorporeal member 23 is connected to the access port 1. The extracorporeal member 23 can be disconnected from the access port 1 by exerting a pressure on the distal ends 24 of the locking members 21. Moreover, the locking members 21 can be used advantageously to allow inserting of the cannulas 74, 75 into the chambers 51, 52 with a predetermined insertion depth, thus diminishing the risk of breaking the cannulas 74, 75 by hitting the bottom of the chambers 51, 52. Here, the predetermined insertion depth, or distance, corresponds to the predetermined position, when the locking ends 25 are engaged with the lower projecting edge 22.

In an embodiment, the insertion depth, or distance, determined by the aligning device 19, 21 can be determined such that the proximal extremity of the end portions 74, 75 contacts substantially the first and second channels 53, 54, as shown in FIG. 3, creating a substantially straight fluidic passage from the first and second access line 71, 72 to the first and second tube lines 41, 42, respectively. Other insertion distances are however possible, for example comprising the proximal extremity of the end portions 74, 75 being flush with the surface of the sealing membrane 8 in contact with the chambers 51, 52, or being at a given distance within the chambers 51, 52. The predetermined distance can be determined by the position of the lower projecting edge 22 along the access port 1. Alternatively, the outer periphery of the guiding cap 19, or the outer periphery of the casing 3 or valve unit 5, can comprise means, such as a grooved or protruding profile, for locking the locking ends 25 at the predetermined position. Alternatively, the locking ends 25 can be formed from a grooved or protruding profile on the inside face of the locking members 21 or simply by friction forces of the locking members 21 on the outer periphery of the guiding cap 19, casing 3 or valve unit 5.

FIG. 3 shows a cross-section view of the access port 1 and the extracorporeal conduit 7, where only one access line 71, one cannula 74, and one chamber 51 are visible. In accordance with this embodiment, the locking mechanism comprises a cap-shaped locking member 21 arranged for example, for clipping its curved locking end 25 on the cap 19 as described above. Here the locking member 21 can also act as the aligning device, by axially aligning the cannula 74 with the chamber 51, and/or with the preformed passage 9, during connection of the connecting member 23 and extracorporeal conduit 7, when the locking end 25 slide along the outer wall of the cap 19, or the upper end 18 of the fixation unit 3 in the absence of cap 19. The locking member 21 can also be arranged to align the cannula 74 angularly, for example, by containing ribs (not shown) forcing the locking member 21 to take an determined angular position during the connection of the extracorporeal conduit to the access port 1. Moreover, when the extracorporeal connecting member 23 is connected, the cap-shaped locking member 21 of the embodiment of FIG. 3 covers the valve unit 5, protecting the latter from possible external contaminations.

In another embodiment not represented, a protective sheet can be inserted, for example glued, on the top surface of the sealing membrane 8, for example, between the sealing membrane 8 and the guiding cap 19, when the access port 1 is unused. The protective sheet allows for preserving the sterile environment of the access port 1. The protective sheet can be removed before connecting the access port 1 to the extracorporeal conduit 7, and reinserted after use.

The disclosure is susceptible to various modifications and alternative forms, and specific examples thereof have been shown by way of example in the drawings and are herein described in detail. It should be understood, however, that the disclosure is not to be limited to the particular forms or methods disclosed, but to the contrary, the disclosure is to cover all modifications, equivalents, and alternatives.

For example, the fixation unit 3 can comprise a central bone screw (not represented) extending axially along the longitudinal axis of the access port 1, the bone screw being not necessarily hollow. In this latter configuration, the internal conduit 4 may exit the valve unit 5 substantially perpendicularly to the valve unit longitudinal axis and, therefore, to the screw. This configuration allows attaching the internal conduit 4 in a direction that is substantially parallel to the upper surface of an underlying bone 100, for example, between the skin 200 and the bone 100. Here, the bone need not necessarily be perforated to pass the internal conduit 4. It is clear that it is also possible to use the base plate 31 as shown in FIG. 1 while allowing the tubing 4 to be oriented laterally to the casing 2. Here, the extracorporeal conduit 7 can exit the valve unit 5 making an angle comprised between 0° and 90° with the valve unit longitudinal axis.

In the example of FIG. 2, the access lines 71, 72 and tube lines 41, 42 are shown packaged in a single extracorporeal and internal conduit 7, 4, respectively. However, the lines 41, 42, 71, 72 could be packaged separately.

The access port system disclosed herein can be used with the extracorporeal conduit 7 and internal conduit 4 containing only one or more than two access and tube lines, respectively, and the access port 1 comprising only one or more than two chambers. For example, an application requiring only one tube line and single access line may be used for urinary catheterism where fluid is removed only. The valve unit 5 can comprise a number of chambers in accordance with the number of access lines and tube lines, respectively, for example, to provide one chamber per access and/or tube line. Obviously, the device can alternatively comprise more than one extracorporeal conduit 7 and more than one internal conduit 4, each with one or more separate access lines or tube lines, respectively.

The disclosed implanted port 1 is suited for numerous applications in therapy, diagnosis or long-term assistance of patients suffering from various diseases or disabilities. For example, the access port 1 can be used to perform haemodialysis. For such application, the internal conduit 4 is connected to a patient's blood vessel, e.g. the internal jugular vein, subclavicular vein, vena cava. Externally, the access port 1 is connected via the extracorporeal conduit 7 to a hemodialysis machine. Using such configuration, blood can be transferred at high flow (50-600 ml/min, or more specific 170-400 ml/min, or even more specific 220-350 ml/min) to the dialysis machine and, after purification, can be returned to the patient. The stable fixation of the access port 1 in the bone 100 allows the use of the access port 1 for the extended time period as 4 to 6, often 8 hours usually required for the hemodialysis treatment. After completion of the dialysis cycle the access port 1 can be closed, cleaned and capped as described above. The access port 1 can be reused many times with no need to perforate skin and vessels with needles for every single cycle. The access port 1 according to the embodiments is especially well suited for large fluid volumes as well as comprising the removal of body fluids. The diameter of the lines 41, 42, 71 and 72 can be between 0.5-1.5 mm, especially between 0.7-1.2 mm, preferably around 1 mm. This enables said fluid rates of 200 to 400 ml/min with the exerted pressure, e.g. 200 mmHg, being a combination of the blood pressure of a patient and the hemodialysis pump, the pressure being applied in both directions, i.e. for removal as well as for the re-introduction of the patient's blood.

A further application refers to the continuous application of drugs that can be delivered in liquid form to any blood vessel, body lumen or organ. Such drugs may be chemotherapeutic agents for tumor therapy. The device can be used to deliver these drugs, for example, to the blood, the cerebrospinal fluid or the peritoneal cavity. Patients suffering from gastrointestinal diseases or disabilities can receive parenteral nutrition applied through the device to the blood. For diabetic patients, the administration of insulin may be facilitated because permanent access to the subcutaneous tissue is granted with this device. Simultaneous application of multiple drugs is also possible with this single device, as is described above.

Another application may be the removal of pathologic fluid anywhere in the body, e.g. from the peritoneum in case of recurrent effusions. Also, long time urinary catheterism can be based on a device accessing the bladder.

REFERENCE NUMBERS 1 transcutaneous implantable access port
2 casing
3 fixation unit
31 base plate
33 threaded structure
4 internal conduit
41 first tube line
42 second tube line
5 valve unit
51 first chamber
52 second chamber
53 first channel
54 second channel
6 open end of the first and second chambers
7 extracorporeal conduit
71 first access line
72 second access line
74 first cannula
75 second cannula
8 flexible sealing membrane
9 first preformed passage
10 second preformed passage
15 chuck cone
16 dimple
17 seat
18 upper end of the fixation unit
19 guiding cap
20 guiding passages
21 locking device
22 lower projecting edge of the guiding cap
23 connecting member
24 distal end of the locking member
25 locking end
100 bone
110 hole drilled in the bone
200 skin

The invention claimed is:

1. An transcutaneous implantable access port for removal and/or return of fluids of a patient comprising:
   a fixation unit adapted to be fixed to a bone of the patient;
   a valve unit comprising a sealing membrane at its distal end and one or more chambers adjacent of said sealing membrane, the valve unit being detachably mounted on the fixation unit such that the distal end of the valve unit protrudes extracorporealy;
   an internal conduit fluidly connectable to a vascular structure of the patient and releasably connectable to the valve unit such as to establish fluidic communication between the internal conduit and said one or more chambers; and
   an extracorporeal connecting member having an end portion;
   said extracorporeal connecting member is adapted to be connected to the distal end of the valve unit such that said end portion passes through said sealing membrane such as to open a fluidic passage between the connecting member, and said one or several chambers and whereby said fluidic passage closes when the connecting member is respectively connected to the access port and withdrawn therefrom.

2. The access port according to claim 1, wherein the access port further comprises an aligning device arranged for inserting the end portion in said one or several chambers according to a predetermined insertion distance, when said extracorporeal connecting member is connected to the valve unit.

3. The access port according to claim 2, wherein said aligning device comprises a guiding element adapted to align the portion of said one or more access lines relative to said one or several chambers, respectively.

4. The access port according to claim 3, wherein said guiding element is a guiding cap containing one or several guiding passages aligned with each of said one or several chambers.

5. The access port according to claim 4, wherein said one or several guiding passages have a tapered shape.

6. The access port according to claim 2, wherein said aligning device comprises a locking device attached to the connecting member.

7. The access port according to claim 6, wherein said locking device comprises a locking member having a locking end adapted to slidably engage along the lateral periphery of the valve unit.

8. The access port system according to claim 1, wherein said sealing membrane is made of silicone rubber or a self-repairing polymer.

9. The access port system according to claim 1, wherein said sealing membrane comprises one or several preformed passage, each of said one or several preformed passages being connected with one of said one or several chambers, respectively.

10. The access port system according to claim 9, wherein said aligning device is adapted to align the end portion relative to one of said one or several preformed passages, respectively.

11. The access port system according to claim 1, wherein said internal conduit contains one or more tube lines, each of said one or more tube lines being fluidly connected to one of said one or more chambers, respectively.

12. The access port system according to claim 1, wherein said extracorporeal connecting member is adapted to be connected to an extracorporeal conduit comprising one or several access lines in fluid communication with the end portion, respectively.

13. The access port system according to claim 1, wherein the fixation unit is a base plate.

14. The implantable access device system of claim 1, wherein the fixation unit comprises a three-dimensional structure.

15. The access port system according to claim 1, wherein said end portion comprises a cannula.

16. An transcutaneous implantable access port for removal and/or return of fluids of a patient comprising:
  a fixation unit adapted to be fixed to a bone of the patient;
  a valve unit comprising a sealing membrane at its distal end and one or more chambers adjacent of said sealing membrane, the valve unit being detachably mounted on the fixation unit such that the distal end of the valve unit protrudes extracorporealy;
  an internal conduit fluidly connectable to a vascular structure of the patient and releasably connectable to the valve unit such as to establish fluidic communication between the internal conduit and said one or more chambers; and
  an extracorporeal connecting member having an end portion;
  said extracorporeal connecting member having an end portion which is adapted such that it can penetrate said sealing membrane to open a fluidic passage between the connecting member and said one or several chambers, so as to open the valve unit; and wherein the sealing member is further configured such that it can self-seal, when the extracorporeal connecting member is removed from penetrating the sealing member so that said fluidic passage closes, so as to close the valve unit.

* * * * *